United States Patent
Kobayashi et al.

(10) Patent No.: US 9,884,162 B2
(45) Date of Patent: Feb. 6, 2018

(54) OXYGEN CONCENTRATION DEVICE

(71) Applicant: Teijin Pharma Limited, Chiyoda-ku, Tokyo (JP)

(72) Inventors: Sumihiro Kobayashi, Yamaguchi (JP); Hisashi Kiriake, Yamaguchi (JP)

(73) Assignee: Teijin Pharma Limited, Tokyo (JP)

( * ) Notice: Subject to any disclaimer, the term of this patent is extended or adjusted under 35 U.S.C. 154(b) by 397 days.

(21) Appl. No.: 14/422,458

(22) PCT Filed: Sep. 19, 2013

(86) PCT No.: PCT/JP2013/076168
§ 371 (c)(1),
(2) Date: Feb. 19, 2015

(87) PCT Pub. No.: WO2014/046297
PCT Pub. Date: Mar. 27, 2014

(65) Prior Publication Data
US 2015/0217078 A1    Aug. 6, 2015

(30) Foreign Application Priority Data
Sep. 20, 2012 (JP) .................................. 2012-207114

(51) Int. Cl.
*A61M 16/10* (2006.01)
*A61M 16/00* (2006.01)
(Continued)

(52) U.S. Cl.
CPC ...... *A61M 16/101* (2014.02); *A61M 16/0003* (2014.02); *A61M 16/0063* (2014.02);
(Continued)

(58) Field of Classification Search
CPC .................................................. A61M 16/101
See application file for complete search history.

(56) References Cited

U.S. PATENT DOCUMENTS 4,605,425 A * 8/1986 Verrando ........... B01D 53/0454
                                                    95/10
5,529,607 A * 6/1996 Tan ..................... B01D 53/047
                                                    95/100
(Continued)

FOREIGN PATENT DOCUMENTS

CN    102665812 A    9/2012
DE    29605889 U1    6/1996
(Continued)

OTHER PUBLICATIONS

Machine translation of WO Pub. 2011/052803 A1 (Ando et al.).*
(Continued)

*Primary Examiner* — (Jackie) Tan-Uyen T Ho
*Assistant Examiner* — Joseph D Boecker
(74) *Attorney, Agent, or Firm* — Sughrue Mion, PLLC (57) ABSTRACT

An oxygen concentration device is provided which, when the number of revolutions of a compressor reaches an upper limit of control, increases an oxygen concentration, and can extend an operating time of the oxygen concentration device, comprising a control means which controls the number of revolutions of the compressor based on a detected value of an oxygen concentration sensor, judges deterioration due to moisture absorption based on the detected value of the oxygen concentration sensor, a detected value of a pressure sensor, and an operating time of an adsorption cylinder and, when criteria for judgment of the deterioration due to moisture absorption are satisfied, makes a purge step time shorter than an initially set time.

5 Claims, 5 Drawing Sheets

(51) Int. Cl.
*A61M 16/20* (2006.01)
*B01D 53/047* (2006.01)
*B01D 53/30* (2006.01)

(52) U.S. Cl.
CPC ........... *A61M 16/20* (2013.01); *B01D 53/047* (2013.01); *B01D 53/30* (2013.01); *A61M 16/107* (2014.02); *A61M 2016/0027* (2013.01); *A61M 2016/1025* (2013.01); *A61M 2202/0208* (2013.01); *A61M 2202/0266* (2013.01); *A61M 2205/3331* (2013.01); *B01D 2253/108* (2013.01); *B01D 2256/12* (2013.01); *B01D 2257/102* (2013.01); *B01D 2259/402* (2013.01); *B01D 2259/40007* (2013.01); *B01D 2259/40052* (2013.01); *B01D 2259/4533* (2013.01)

(56) References Cited

U.S. PATENT DOCUMENTS

| | | | |
|---|---|---|---|
| 5,593,478 A | 1/1997 | Hill et al. | |
| 5,906,672 A * | 5/1999 | Michaels | B01D 53/047 95/12 |
| 5,917,135 A * | 6/1999 | Michaels | B01D 53/047 95/101 |
| 7,491,264 B2 | 2/2009 | Tao et al. | |
| 8,636,838 B2 | 1/2014 | Watanabe et al. | |
| 8,753,435 B2 * | 6/2014 | Atlas | A61M 16/10 128/204.18 |
| 9,011,582 B2 | 4/2015 | Ando et al. | |
| 2002/0096174 A1 * | 7/2002 | Hill | A61M 16/10 128/205.11 |
| 2005/0045041 A1 | 3/2005 | Hechinger et al. | |
| 2006/0230924 A1 * | 10/2006 | Deane | B01D 53/053 95/22 |
| 2006/0230929 A1 * | 10/2006 | Bliss | B01D 53/0407 95/96 |
| 2007/0214955 A1 * | 9/2007 | Aylsworth | B01D 53/0454 95/19 |
| 2007/0227360 A1 * | 10/2007 | Atlas | A61M 16/10 96/121 |
| 2008/0047426 A1 * | 2/2008 | Dolensky | A62B 21/00 95/22 |
| 2011/0232483 A1 * | 9/2011 | Haberland | A61M 16/10 95/23 |
| 2012/0272966 A1 | 11/2012 | Ando et al. | |
| 2013/0125746 A1 * | 5/2013 | Manning | B01D 53/0473 95/19 |

FOREIGN PATENT DOCUMENTS

| | | |
|---|---|---|
| EP | 2497516 A1 | 9/2012 |
| JP | 2000516854 A | 12/2000 |
| JP | 2002253675 A | 9/2002 |
| JP | 2008-061929 A | 3/2008 |
| JP | 2008-113862 A | 5/2008 |
| JP | 2008-125885 A | 6/2008 |
| JP | 2009219990 A | 10/2009 |
| TW | 200536576 A | 11/2005 |
| TW | 201124180 A | 7/2011 |
| TW | 201127429 A | 8/2011 |
| WO | 2011/052803 A1 | 5/2011 |

OTHER PUBLICATIONS

International Search Report of PCT/JP2013/076168 dated Nov. 12, 2013.
Communication dated Sep. 9, 2015, issued by the European Patent Office in corresponding European Application No. 13839172.7.
Office Action dated Jan. 4, 2016 issued by the State Intellectual Property Office of the People's Republic of China in corresponding CN Appln. No. 201380049091.1 (12 pages, including machine translation).

* cited by examiner

Ad cylinder: Adsorption cylinder

| Ad cylinder A | Desorption | Purge/Exhaust | Adsorption | Purge/Generation |
|---|---|---|---|---|
| Ad cylinder B | Adsorption | Purge/Generation | Desorption | Purge/Exhaust |

Supply valve A: Open/Close
Exhaust valve A: Open/Close
Supply valve B: Open/Close
Exhaust valve B: Open/Close
Pressure equalizing valve: Open/Close

| Ad cylinder A | Pressure equalizing | Desorption | Purge/Exhaust | Pressure equalizing | Adsorption | Purge/Generation |
|---|---|---|---|---|---|---|
| Ad cylinder B | | Adsorption | Purge/Generation | | Desorption | Purge/Exhaust |

Supply valve A: Open/Close
Exhaust valve A: Open/Close
Supply valve B: Open/Close
Exhaust valve B: Open/Close
Pressure equalizing valve: Open/Close

OXYGEN CONCENTRATION DEVICE

CROSS REFERENCE TO RELATED APPLICATIONS

This is a National Stage of International Application No. PCT/JP2013/076168 filed Sep. 19, 2013, claiming priority based on Japanese Patent Application No. 2012-207114 filed Sep. 20, 2012, the contents of all of which are incorporated herein by reference in their entirety.

TECHNICAL FIELD

The present invention relates to a pressure swing adsorption-type oxygen concentration device using an adsorbent which preferentially adsorbs nitrogen relative to oxygen. More specifically, the present invention relates to a medical oxygen concentration device used for oxygen inhalation therapy that is performed for a patient with chronic respiratory disease and the like.

BACKGROUND ART

In recent years, the number of patients suffering from respiratory system diseases such as asthma, pulmonary emphysema, chronic bronchitis and the like has tended to increase. One of the most effective therapeutic methods for these diseases is oxygen inhalation therapy. In such oxygen inhalation therapy, oxygen gas or oxygen-enriched gas is inhaled by patients. An oxygen concentration device, liquid oxygen or oxygen gas cylinder, and the like are known as an oxygen supply source used for the oxygen inhalation therapy. However, an oxygen concentration device is mainly used for home oxygen therapy because it is convenient to use and easy for maintenance and management.

An oxygen concentration device is a device to supply oxygen to a user by separating and concentrating oxygen that makes up 21% of the air. As such device, there are a membrane-type oxygen concentration device that uses a membrane which selectively permeate oxygen and a pressure swing adsorption-type oxygen concentration device that uses an adsorbent which can preferentially adsorbs nitrogen or oxygen. A pressure swing adsorption-type oxygen concentration device is mainly used because it can obtain highly concentrated oxygen.

The pressure swing adsorption-type oxygen concentration device continuously produces a highly concentrated oxygen gas by repeating alternately a compression-adsorption step and a decompression-desorption step. In the former step, un-adsorbed oxygen is obtained by supplying air compressed by a compressor to an adsorption cylinder filled with an adsorbent which selectively adsorbs nitrogen relative to oxygen, such as 5A, 13X, or Li—X type molecular sieve zeolites, and adsorbing nitrogen under pressurized conditions. In the latter step, the adsorbent is regenerated by purging nitrogen adsorbed on the adsorbent under a reduced pressure of atmospheric pressure or less in the adsorption cylinder.

CITATION LIST

Japanese Unexamined Patent Application Publication No. 2002-253675
Japanese Unexamined Patent Application Publication No. 2000-516854

SUMMARY OF INVENTION

Technical Problem

In a pressure swing adsorption-type oxygen concentration device, moisture contained in raw material air is adsorbed on an adsorbent and, because of temporal deterioration of the adsorbent due to moisture absorption, decrease in the oxygen concentration is brought about. In order to compensate for the decrease in the oxygen concentration, the pressure swing adsorption-type oxygen concentration device which supplies oxygen at a constant concentration is configured to carry out control to increase the oxygen concentration by increasing pressure in an adsorption cylinder by increasing the number of revolutions of a compressor (as described in Japanese Unexamined Patent Application Publication No. 2002-253675). However, there is a limit to compensating for the decrease in the oxygen concentration by increasing the number of revolutions of the compressor.

In order to compensate for a temporal change in the concentration of oxygen generated and the decrease in the oxygen concentration due to temporal deterioration of the device, and to maintain the constant oxygen concentration, there is also known a device which maintains the oxygen concentration of a product gas by detecting the oxygen concentration of an oxygen-concentrated gas by an oxygen sensor and carrying out feedback control of an air feed rate of the compressor, an adsorption/desorption cycle time, and the like (as described in Japanese Unexamined Patent Application Publication No. 2000-516854). However, alteration of a switching cycle time of the adsorption/desorption step time causes a temporary variation of the oxygen concentration, and it takes time for the concentration to reach a preset value. Thus, this method tends to lack stable control.

The present inventors have found that an optimum time of a purge step, where a part of oxygen generated in an adsorption step is passed to the adsorption cylinder at a desorption step side to accelerate desorption of nitrogen, shifts to a shorter time side because of deterioration of the adsorbent due to moisture absorption and that, when the number of revolutions of the compressor reaches an upper limit value of control, the oxygen concentration can be increased by making the purge time shorter, thus making it possible to extend the operating time of the oxygen concentration device.

Solution to Problem

The present invention provides the following oxygen concentration device.

1. A pressure swing adsorption-type oxygen concentration device comprising:
    a plurality of adsorption cylinders packed with an adsorbent that selectively adsorbs nitrogen rather than oxygen; a compressor that supplies compressed air to the adsorption cylinder;
    a flow path switching means that repeats, by sequentially switching a flow path between the compressor and each adsorption cylinder, at a prescribed timing, an adsorption step where pressurized air is supplied to each adsorption cylinder and an oxygen-concentrated gas is taken out, a desorption step where each adsorption cylinder is decompressed and the adsorbent is regenerated, and a purge step where the oxygen-concentrated gas from an adsorption cylinder at an adsorption step side is introduced to an adsorption cylinder at a desorption step side;

a flow rate setting means that supplies the oxygen-concentrated gas by adjusting the flow rate to a desired value; and a control means that controls operation of an oxygen concentration sensor to measure a concentration of the oxygen-concentrated gas, a pressure sensor to detect a pressure of the adsorption cylinder, the compressor and the flow path switching means, wherein the control means controls the number of revolutions of the compressor based on a detected value of the oxygen concentration sensor, judges deterioration of the adsorbent due to moisture adsorption based on the detected value of the oxygen concentration sensor, a detected value of the pressure sensor, and an operating time of the adsorption cylinder, and when criteria for judgment of deterioration due to moisture absorption are satisfied, controls a switching time of the flow path switching means so that a time for the purge step becomes shorter than an initially set value.

2. The oxygen concentration device according to paragraph 1, wherein the criteria for judgment of the deterioration due to moisture absorption are to satisfy all three conditions: that the detected value of the oxygen concentration sensor is not more than a prescribed concentration value; that the number of revolutions of the compressor is an upper limit value of control and the detected value of the pressure sensor is not less than a pressure value at an initial stage of use of the device when the compressor is revolving under said condition; and that the operating time of the adsorption cylinder is not less than a prescribed time.

3. The oxygen concentration device according to paragraph 1, wherein the criteria for judgment of the deterioration due to moisture absorption are to satisfy all three conditions: that the detected value of the oxygen concentration sensor is not more than a prescribed concentration value; that the number of revolutions of the compressor is the number of revolutions of the compressor at a maximum flow rate set value and the detected value of the pressure sensor is not less than a pressure value at an initial stage of use of the device when the compressor is revolving under said condition; and that the operating time of the adsorption cylinder is not less than a prescribed time.

4. The oxygen concentration device according to paragraph 2 or paragraph 3, wherein when, after controlling the switching time of the flow path switching means so that the time of the purge step becomes shorter than an initially set time by satisfying the criteria for judgment of the deterioration due to moisture absorption, the criteria are satisfied again, the switching time of the flow path switching means is controlled so that the time of the purge step becomes shorter than the set time of the previous control.

5. The oxygen concentration device according to any one of paragraphs 2 to 4, wherein the detected value of the oxygen concentration sensor is 90% or less and the operating time of the adsorption cylinder is 2000 hours or more.

Advantageous Effects of Invention

According to the oxygen concentration device of the present invention, the oxygen concentration can be increased rapidly in response to a decrease in nitrogen adsorption performance caused by the temporal deterioration of the adsorbent and an accompanying decrease in the oxygen concentration of the oxygen-concentrated gas. Thus, an oxygen concentration device that enables long-term use can be provided.

DESCRIPTION OF EMBODIMENTS

An embodiment of an oxygen concentration device of the present invention will be described with reference to the drawings below.

Figure 1:
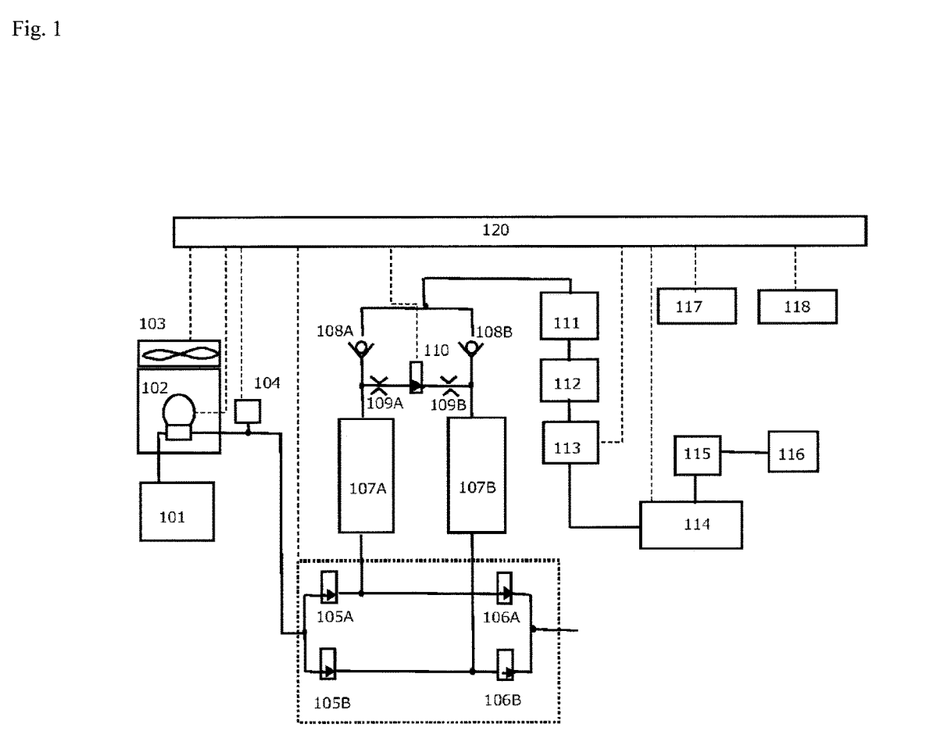
FIG. 1 is a schematic diagram showing a pressure swing adsorption-type oxygen concentration device according to an embodiment of the oxygen concentration device of the present invention. Further.

FIG. 1 is a schematic constitutional diagram showing the pressure swing adsorption-type oxygen concentration device according to one embodiment of the present invention. The oxygen concentration device of the present invention comprises: a compressor 102 which supplies compressed air; adsorption cylinders 107A and 107B packed with an adsorbent which selectively adsorbs nitrogen rather than oxygen; and supply valves 105A and 105B, exhaust valves 106A and 106B, and a pressure equalizing valve 110 which are flow path switching means that switch a sequence of an adsorption step, a desorption step, a pressure equalizing step, and the like. An oxygen-concentrated gas generated by separation from the compressed air is adjusted to a prescribed flow rate by a control valve 113, freed from dust by a filter 115, and thereafter supplied to a user by using a nasal cannula 116.

Raw material air is brought into the oxygen concentration device from outside through an air intake port equipped with an external air intake filter 101 for eliminating foreign matter such as dust and the like. In this case, normal air contains about 21% oxygen gas, about 77% nitrogen gas, 0.8% argon gas, and 1.2% other gases such as carbon dioxide and the like. Such oxygen concentration device enriches an oxygen gas, which is essential for respiration, and extracts it.

To extract the oxygen-concentrated gas, the raw material air compressed by the compressor 102 is supplied to an adsorption cylinder 107 packed with an adsorbent composed of zeolite and the like, which selectively adsorbs nitrogen molecules rather than oxygen molecules, by opening and closing the supply valves 105A and 105B, and the exhaust valves 106A and 106B, while switching the adsorption cylinders 107A and 107B sequentially, and by selectively removing a nitrogen gas contained in the raw material air in the adsorption cylinder at a concentration of about 77%. As such an adsorbent, there can be used molecular sieve zeolite such as Type 5A, Type 13X, Type Li—X, and the like.

The adsorption cylinder 107 is made of a cylindrical container packed with an adsorbent, and usually used are a one-cylinder type, a two-cylinder type and, in addition, a multi-cylinder type such as a three- or more-cylinder type. However, in order to produce the oxygen-concentrated gas continuously and efficiently from the raw material air, it is desirable to use an adsorption cylinder of a two-cylinder type or a multi-cylinder type.

The compressor 102 may have merely a compressing function or both compressing and evacuating functions, and may be a two-head type swing air compressor as well as a rotational air compressor such as screw type, rotary type, scroll type and the like. Either alternating current or direct current may be used as a power source of an electric motor for driving the compressor.

In the adsorption cylinder in a compressed state, nitrogen in the air is adsorbed by the adsorbent, and the oxygen-concentrated gas containing oxygen as a main component, which was not adsorbed, is taken out from a product exit side of the adsorption cylinder and flows into a product tank 111 via check valves 108A and 108B which are installed to prevent the oxygen-concentrated gas from flowing back into the adsorption cylinder.

On the other hand, the nitrogen gas adsorbed by the adsorbent packed in the adsorption cylinder needs to be desorbed from the adsorbent and purged, in order for the adsorbent to adsorb nitrogen again from newly introduced raw material air. For this purpose, the adsorption cylinders 107A and 107B are connected to an exhaust line via the exhaust valves 106A and 106B, and a compressed state is switched to a state open to the air, thereby desorbing nitrogen adsorbed in a compressed state and discharging the same into the air to regenerate the adsorbent. Furthermore, in this desorption step, a purge step is performed in order to improve the efficiency of nitrogen desorption, wherein a part of the oxygen-concentrated gas generated is flowed back as a purging gas from the product exit side of the adsorption cylinder in the adsorption step to the adsorption cylinder in the desorption step via orifices 109A and 109B, and the pressure equalizing valve 110.

The oxygen-concentrated gas stored in the product tank 111 contains oxygen having a high concentration of, for example, 95%, and a necessary oxygen flow rate is set by a patient himself according to a doctor's prescription. A prescribed amount of the concentrated oxygen gas is supplied to the patient with pressure and a supply flow rate thereof controlled by means of a flow rate adjusting means such as a pressure regulating valve 112, a control valve 113, and the like. On the other hand, the flow rate and the oxygen concentration of the oxygen-concentrated gas supplied to the patient are detected by an oxygen concentration sensor/flow rate sensor 117 and, based on detection results, the number of revolutions of the compressor 102, and an opening/closing times of the flow path switching means such as the supply valve 105, the exhaust valve 106, and the pressure equalizing valve 110 are controlled by an operating means such as CPU 120 and the like to control generation of oxygen.

The adsorption pressure is measured in terms of internal pressure of the adsorption cylinder or discharge pressure of the compressor, and is detected by a pressure sensor, as shown in FIG. 1, installed on a pipe at a discharge side of the compressor or a pressure sensor installed on the adsorption cylinder.

Figure 2:
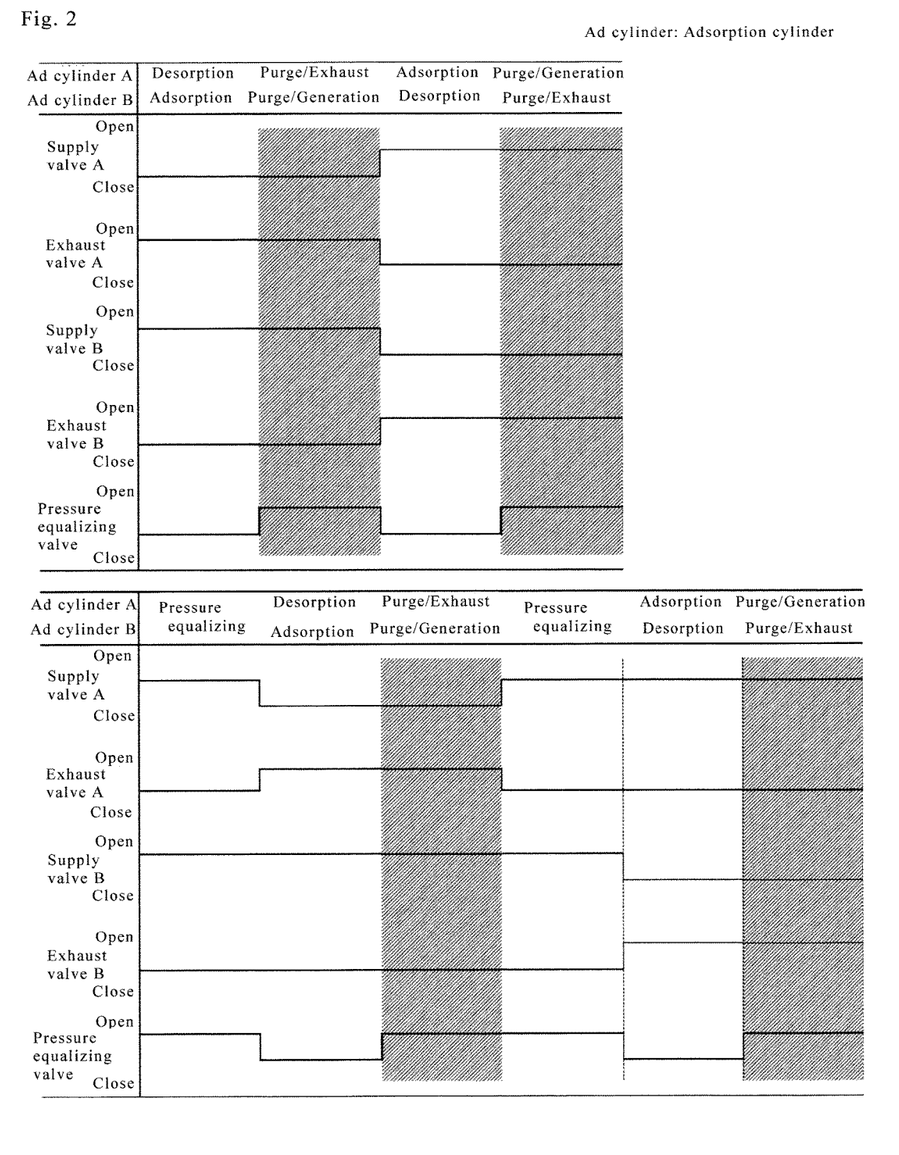
FIG. 2 represents opening/closing switching timing of supply valves, exhaust valves and a pressure-equalizing valve in respective steps of adsorption/desorption of the pressure swing adsorption-type oxygen concentration device of the present invention.

FIG. 2 is a schematic diagram of opening/closing timing of the flow path switching means according to one embodiment of the oxygen concentration device of the present invention, with which sequentially switched are the supply valves and the exhaust valves installed on a flow path between the compressor and each adsorption cylinder, and a pressure equalizing valve which equalizes pressure between the adsorption cylinders at a downstream side of the adsorption cylinders.

In the two-cylinder pressure swing adsorption-type oxygen concentration device, as shown in FIG. 2, while the adsorption cylinder A is performing the adsorption step, the adsorption cylinder B performs the desorption step. The adsorption step and desorption step are sequentially switched and the steps of the cylinders A and B are in opposite phase to each other to continuously produce oxygen by controlling opening/closing of the supply valves A and B, the exhaust valves A and B, and the pressure equalizing valve.

Oxygen can be produced efficiently by incorporating a purge step in which a part of the oxygen generated in the adsorption step is passed to the adsorption cylinder at the desorption step side via the pressure equalizing valve in order to improve efficiency in regenerating the adsorbent, and by carrying out a stationary sequence of switching steps in cylinders A and B, wherein a series of the adsorption step, a purge-generation step, the desorption step, and a purge-exhaust step in the adsorption cylinder A and a series of the desorption step, the purge-exhaust step, the adsorption step, and the purge-generation step in the adsorption cylinder B are performed alternately.

As shown in the shaded portion of FIG. 2, the purge step is, for example, to extract oxygen from the adsorption cylinder B producing oxygen in the adsorption step, simultaneously to pass a part of the oxygen produced through the pressure equalizing valve to the adsorption cylinder A evacuating nitrogen in the desorption step, and consequently to improve the efficiency of the nitrogen desorption and regeneration of the adsorbents. In the adsorption cylinder B, the purge-generation step is carried out to generate oxygen for purging, while in the adsorption cylinder A, a purge-discharge step is carried out to flow the oxygen from the product exit side as a purging gas, which is then discharged outside.

When the length of the purge step is large, the regeneration efficiency of the adsorbents is improved, resulting in an increase in the oxygen concentration of the oxygen-enriched gas produced. On the other hand, when a purge step time is made too long, the amount of oxygen taken out from the adsorption cylinder B to the product tank side decreases, and moreover, depending on the amount taken out, a decrease in the concentration of oxygen generated may be caused by nitrogen breakthrough, resulting in a demerit that the generated amount of the product gas decreases. When the whole sequence including changes of the length of an adsorption step or desorption step is controlled, the whole sequence may become imbalanced, requiring a certain time for the stabilization of the oxygen concentration of the oxygen-enriched gas produced. Accordingly, the length of the purge step is controlled in the present invention.

By using the oxygen concentration device for a long time, the adsorbent deteriorates by moisture absorption, which causes a decrease in the oxygen concentration of the oxygen-concentrated gas generated. The molecular sieve zeolite used as a nitrogen absorbent has strong moisture adsorbing ability, and the moisture adsorbed by the adsorbent cannot be removed completely during the desorption step and the purge step, thus causing deterioration of the nitrogen adsorption performance. Usually, in order to compensate for such a decrease in the oxygen concentration, control is carried out to increase the oxygen concentration by increasing the number of revolutions of the compressor of the oxygen concentration device, increasing the amount of the raw material air supplied, and increasing the pressure in the adsorption cylinder.

Optimization of the purge time was examined in order to respond to the decrease in the oxygen concentration of the oxygen-concentrated gas generated, caused by deterioration due to moisture absorption.

Figure 3:
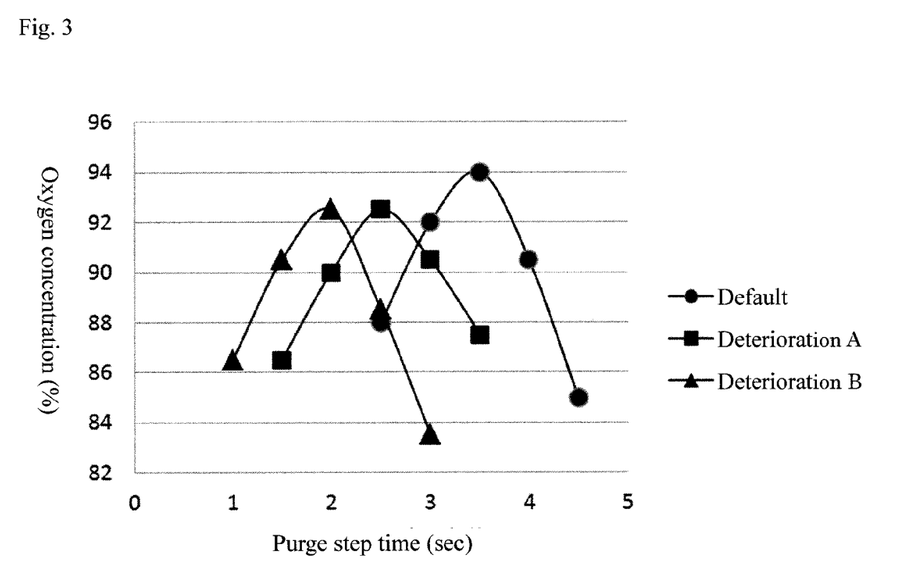
FIG. 3 represents a relationship between a decrease in the oxygen concentration caused by the deterioration of the adsorbent due to moisture absorption and a purge time. Furthermore.

As shown in FIG. 3, the optimum value of the purge time decreases to the shorter time side with deterioration of the adsorbent due to moisture absorption. Thus, an increase in the oxygen concentration can be attempted by decreasing the purge time to cope with (for compensating) the deterioration due to moisture absorption. Namely, for an initially preset value of the purge time of 3.5 seconds, the purge time is shortened to 2.5 seconds and then to 2.0 seconds as the temporal deterioration progresses to the deterioration A and to B, respectively. Therefore, by changing the purge time to a shorter time side, the oxygen concentration increases. When changing the purge time to a shorter time side in this way, it is preferable not to shorten the time to an optimum value all at once but to gradually change the time at such small intervals as 0.1 second and 0.2 second, because, in this way, there is less effect on the concentration of oxygen generated.

When a cycle time of the adsorption/desorption step is changed carelessly without considering a reason of the decrease in the oxygen concentration, there will be incurred destabilization of oxygen generation. It is important to carry out control of shifting the purge time to a prescribed shorter time side after judging from a plurality of parameters that deterioration due to moisture absorption is occurring and by understanding in advance that the decrease in the oxygen concentration of the oxygen-concentrated gas is caused by the deterioration of the adsorbent due to moisture absorption.

The deterioration of the adsorbent due to moisture absorption is accompanied by phenomena that the concentration of the oxygen-concentrated gas generated decreases to a prescribed concentration or lower and that the adsorption pressure increases to a prescribed value or higher. A threshold value of the oxygen concentration is preferably set between 90% or less and a minimum value of the oxygen-concentrated gas or more, wherein the minimum value is guaranteed by the oxygen concentration device. For example, in the case of a medical oxygen concentration device that supplies a high concentration oxygen-concentrated gas, the threshold value is preferably set between 80 and 90%.

Even though the adsorption pressure shows somewhat different values depending on the place of installment of the pressure sensor, as may be seen between the inner pressure of the adsorption cylinder and the discharge pressure of the compressor, either value may be used to carry out control. In the case of the oxygen concentration device, the pressure varies greatly between the adsorption and desorption steps. Furthermore, for purposes of cutting electricity consumption and compensating for the oxygen concentration, control of the number of revolutions of the compressor is carried out according to a preset value of the flow rate. In this case, the number of revolutions of the compressor is feedback-controlled by detecting the oxygen concentration, and the adsorption pressure does not show a constant threshold value. Further, the pressure value varies also by factors other than the deterioration of the adsorbent due to moisture absorption, such as, for example, a decrease in the adsorption pressure due to an abnormal failure of the compressor or electromagnetic valves, piping abnormality, and the like.

In order to exclude variation of the adsorption pressure based on factors other than the deterioration of the adsorbent due to moisture absorption, such as normal control of the number of revolutions of the compressor triggered by the preset flow rate, the oxygen concentration, and the like, and equipment abnormality, it is preferable to set conditions as criteria for judgment of deterioration of the adsorbent due to moisture absorption such as 1) that the number of revolutions of the compressor is an upper limit value of control, and a detected value of the pressure sensor is not less than a pressure value set at an initial stage of use of the device when the compressor is revolving under said conditions, or 2) that the number of revolutions of the compressor corresponds to that of the compressor at a maximum preset flow rate value of the flow rate setting means, and a detected value of the pressure sensor is not less than a pressure value set at an initial stage of use of the device when the compressor is revolving under said conditions. It is detected that the adsorption pressure of the device shows a pressure value which is not less than a normal range. In addition, it is also possible to detect an increase in the adsorption pressure based on the initial adsorption pressure under operating conditions of the compressor determined in advance for every set value of the flow rate.

Furthermore, such deterioration of the adsorbent due to moisture absorption occurs as a result of operation of the oxygen concentration device for at least a certain period of time and, if the control of the present invention is activated at a time soon after the start of the device operation, it is suggested that other device abnormality is occurring. Thus, it is a prerequisite for activating the control of the present invention for shifting the purge time to a shorter time side that at least a prescribed time has passed after the start of operation of the adsorption device. Ordinarily, the oxygen concentration device is preferably used in a living environment of, for example, from 5° C. to 35° C., but it may also be used in a severe winter period below the freezing point or under conditions of intense heat of 40° C. or more. The deterioration of the adsorbent due to moisture absorption prominently appears especially in a low temperature environment of, for example, 5° C. or less, and below the freezing point. A rate of deterioration of the adsorbent varies greatly depending on the environment in which the device is used. Therefore, it is preferable that an operating time of the adsorption cylinder has passed at least 500 hours or more, preferably 2000 hours or more before activating the control.

Figure 4:
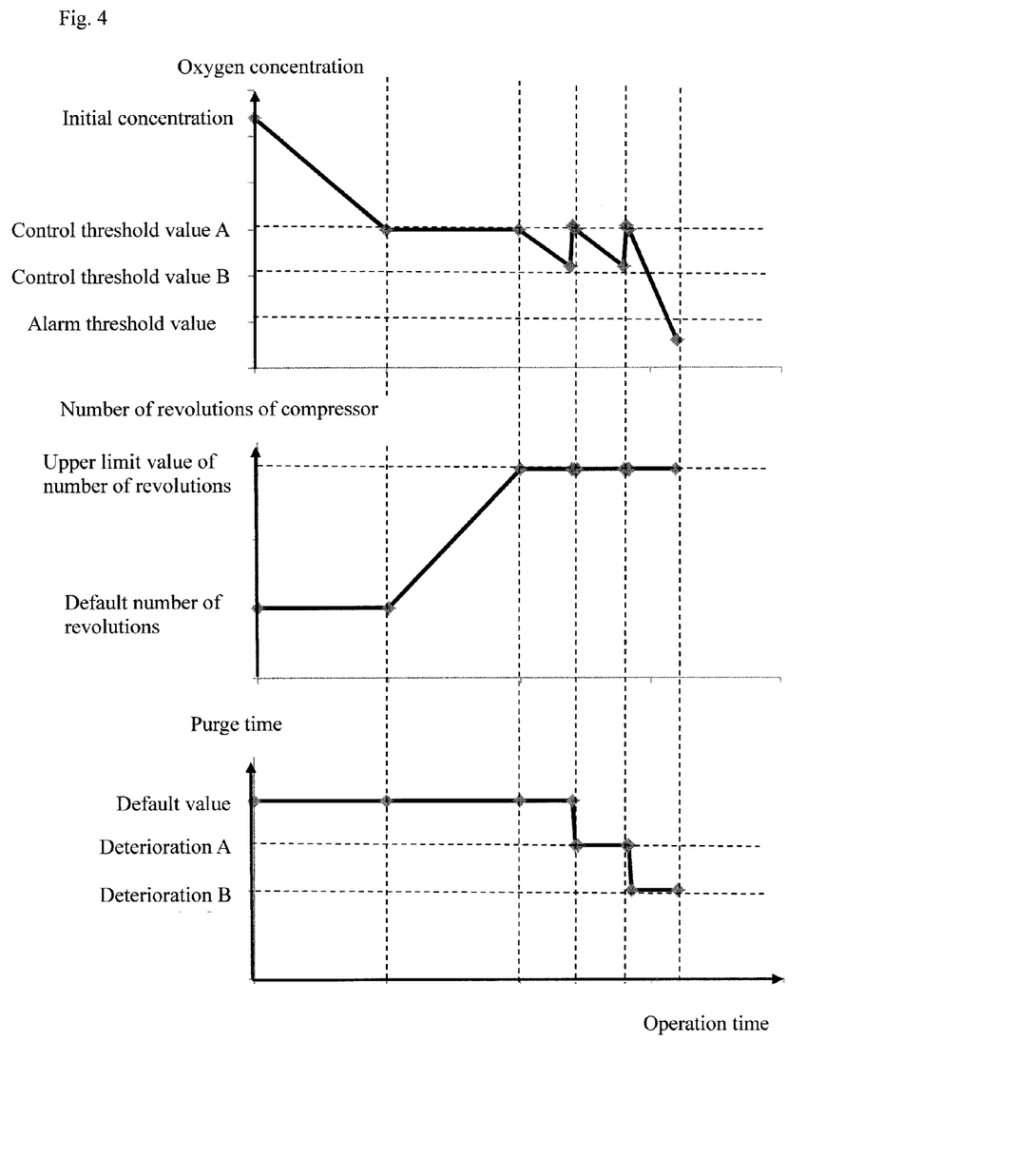
FIG. 4 and FIG. 5 show relationships between a change in the oxygen concentration caused by the temporal deterioration of the oxygen concentration device and control of the number of revolutions of the compressor and control of purge time.
Figure 5:
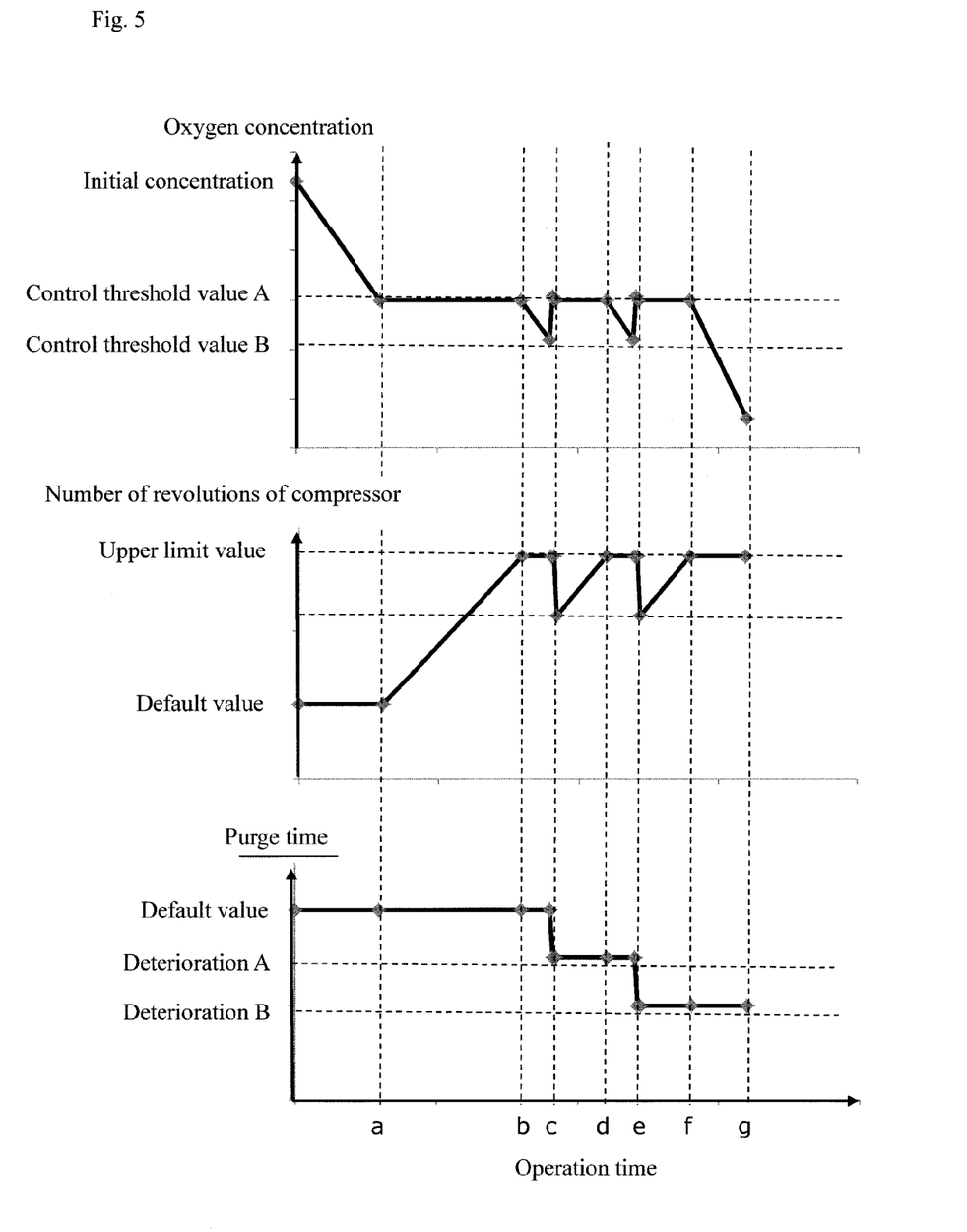

In FIG. 4 and FIG. 5, there are shown relationships between the oxygen concentration of the oxygen-concentrated gas, the number of revolutions of the compressor, and a purge time when, in the oxygen concentration device of the present invention, the purge time shift to a shorter time side is carried out after an oxygen concentration compensation control is performed by increasing the number of revolutions of the compressor due to the decrease in the oxygen concentration of the oxygen-concentrated gas generated, and the control by the number of revolutions of the compressor has reached a limit.

As is shown in FIG. 4, the oxygen concentration shows a value of 95% at an initial stage of operation of the oxygen concentration device, but the oxygen concentration of the oxygen-concentrated gas generated decreases because of the temporal deterioration of the adsorbent due to moisture absorption. At a point of time when the oxygen concentration falls below 90%, the number of revolutions of the compressor is increased and the adsorption pressure is increased to maintain the oxygen concentration at 90%. As the deterioration due to moisture absorption progresses, a control is activated to further increase the number of revolutions of the compressor. However, there is a limit to it and, after the number of revolutions of the compressor reaches an upper limit and, at a point of time when the oxygen concentration falls below 88%, the purge time shift to a shorter time side is carried out (Deterioration A). This causes a temporary increase in the oxygen concentration of the oxygen-concentrated gas generated. As the temporal deterioration progresses further, and when the oxygen concentration falls below 88% again, a control to shift the purge time further to a shorter time side is activated (Deterioration B). This causes another increase in the oxygen concentration of the oxygen-concentrated gas generated.

FIG. 5 shows an example where the oxygen concentration compensation control at Deterioration A and Deterioration B are used simultaneously. The oxygen concentration shows a value of 95% at an initial stage of operation of the oxygen concentration device, but the oxygen concentration of the oxygen-concentrated gas generated decreases because of the temporal deterioration of the adsorbent due to moisture absorption. At a point of time "a" when the oxygen concentration falls below 90%, the number of revolutions of the compressor is increased and the adsorption pressure is increased to maintain the oxygen concentration at 90%. At a point of time "b" when the deterioration due to moisture absorption has progressed further and the number of revolutions of the compressor has reached the upper limit, the oxygen concentration compensation control is terminated. Thereafter, at a point of time "c" when the oxygen concentration falls below 88%, the purge time shift to a shorter time side is carried out (Deterioration A). This causes a temporary increase in the oxygen concentration of the oxygen-concentrated gas generated. With the increase in the oxygen concentration, the oxygen concentration compensation control is resumed and the number of revolutions of the compressor decreases. At a point of time "d" when the deterioration due to moisture absorption has progressed further and the number of revolutions of the compressor has reached the upper limit again, the oxygen concentration compensation control is terminated. And, at a point of time "e" when the oxygen concentration falls below 88% again, a control to shift the purge time further to a shorter time side is activated (Deterioration B). This causes another increase in the oxygen concentration of the oxygen-concentrated gas generated. Thereafter, in the same way as in Deterioration A, the oxygen concentration compensation control is resumed, and a decrease in the number of revolutions of the compressor occurs. Subsequently, the number of revolutions of the compressor reaches the upper limit at a point of time "f", and a decrease in the oxygen concentration occurs.

Regarding such shifting control of the purge time, FIG. 4 and FIG. 5 show examples of activating the control twice. However, by repeating the control from 2 to about 5 times, the concentration of the oxygen generated can be maintained and a long time operation of the oxygen concentration device becomes possible. Determining the setting value for the purge time depends on the generation capacity of the oxygen concentration device, the oxygen concentration supplied, and the like.

At the start-up of the oxygen concentration device, the operation is initiated usually with the purge time set by a default. The deterioration of the adsorbent by moisture absorption is judged based on the above three conditions including the oxygen concentration of the oxygen-concentrated gas generated, the adsorption pressure, and the operating time of the adsorption cylinder(s). For example, when the oxygen concentration is less than 88%, the adsorption pressure when the compressor is operating at a maximum number of revolutions is not less than the initial pressure, and the operating time of the adsorption cylinder is 2000 hours or more, the purge time is changed from 3.5 seconds to 2.5 seconds (Deterioration A). The number of times of the purge time change is stored and, while repeating ON/OFF of the device, when the purge time shift to a shorter time side is carried out, for example, three or more times under the conditions where the three conditions of the deterioration due to moisture absorption are satisfied, the next startup is initiated with a purge time of Deterioration A, i.e. of 2.5 seconds.

Furthermore, when thereafter the three conditions are satisfied again, the purge time is shifted to a shorter time side from 2.5 seconds to 2 seconds as Deterioration B. This causes an increase in the oxygen concentration, and duration of use of the oxygen concentration device can be extended.

INDUSTRIAL APPLICABILITY

The oxygen concentration device of the present invention can be used as a medical oxygen concentration device and particularly as a source of oxygen supply of oxygen inhalation therapy for patients suffering from respiratory system diseases such as asthma, pulmonary emphysema, chronic bronchitis and the like. In addition, the oxygen concentration device can be utilized as a device capable of supplying oxygen with long-term stability that is a characteristic of the present invention.

The invention claimed is:
1. A pressure swing adsorption-type oxygen concentration device comprising:
    a plurality of adsorption cylinders packed with an adsorbent that selectively adsorbs nitrogen rather than oxygen; a compressor that supplies compressed air to the adsorption cylinders;
    a flow path switching means that repeats, by sequentially switching a flow path between the compressor and each adsorption cylinder, at a prescribed timing, an adsorption step where pressurized air is supplied to each adsorption cylinder and an oxygen-concentrated gas is taken out, a desorption step where each adsorption cylinder is decompressed and the adsorbent is regenerated, and a purge step where the oxygen-concentrated gas from an adsorption cylinder at an adsorption step side is introduced to an adsorption cylinder at a desorption step side;
    a flow rate setting means that supplies the oxygen-concentrated gas by adjusting a flow rate to a desired value; and
    a control means that controls operation of an oxygen concentration sensor to measure a concentration of the oxygen-concentrated gas, a pressure sensor to detect a pressure of the adsorption cylinder, the compressor and the flow path switching means,
    wherein the control means controls a speed of revolution of the compressor based on a detected value of the oxygen concentration sensor, judges deterioration of the adsorbent due to moisture absorption based on the detected value of the oxygen concentration sensor, a detected value of the pressure sensor, and an operating time of the adsorption cylinder, wherein the operating time is an accumulated number of hours of usage of the adsorption cylinder, and when criteria for judgment of deterioration due to moisture absorption are satisfied, controls a switching time of the flow path switching means so that a time for the purge step becomes shorter than an initially set value.

2. The oxygen concentration device according to claim 1, wherein the criteria for judgment of the deterioration due to moisture absorption are to satisfy all three conditions: that the detected value of the oxygen concentration sensor is not more than a prescribed concentration value; that the speed of revolution of the compressor is an upper limit value of control and the detected value of the pressure sensor is not less than a pressure value at an initial stage of use of the device when the compressor is revolving at the upper limit value of control; and that the operating time of the adsorption cylinder is not less than a prescribed time.

3. The oxygen concentration device according to claim 1, wherein the criteria for judgment of the deterioration due to moisture absorption are to satisfy all three conditions: that the detected value of the oxygen concentration sensor is not more than a prescribed concentration value; that the speed of revolution of the compressor is the speed of revolution of the compressor at a maximum flow rate set value and the detected value of the pressure sensor is not less than a pressure value at an initial stage of use of the device when the compressor is revolving at the maximum flow rate set value; and that the operating time of the adsorption cylinder is not less than a prescribed time.

4. The oxygen concentration device according to claim 2, wherein when, after controlling the switching time of the flow path switching means so that the time of the purge step becomes shorter than an initially set time, the criteria for judgment of the deterioration due to moisture absorption are satisfied again, the switching time of the flow path switching means is controlled so that the time of the purge step becomes shorter than the set time of the previous control.

5. The oxygen concentration device according to claim 2, wherein the prescribed value of the oxygen concentration sensor is 90% or less and the prescribed operating time of the adsorption cylinder is 2000 hours or more.

* * * * *